United States Patent [19]

Howson et al.

[11] 4,235,242
[45] Nov. 25, 1980

[54] ELECTRONIC CIRCUIT PERMITTING SIMULTANEOUS USE OF STIMULATING AND MONITORING EQUIPMENT

[75] Inventors: David C. Howson; James E. Heule, both of Minneapolis, Minn.

[73] Assignee: Med General, Inc., Minneapolis, Minn.

[21] Appl. No.: 25,857

[22] Filed: Apr. 2, 1979

[51] Int. Cl.³ .............................................. A61B 5/04
[52] U.S. Cl. .................................... 128/695; 128/901
[58] Field of Search .............. 128/695, 696, 697, 700, 128/708, 709, 710, 908, 419 PT, 421, 422, 423, 901, 902

[56] References Cited

U.S. PATENT DOCUMENTS

| | | | |
|---|---|---|---|
| 2,622,150 | 12/1952 | Coulter et al. | 128/695 |
| 3,580,241 | 5/1971 | Weinstein | 128/710 |
| 3,628,538 | 12/1971 | Vincent | 128/422 |
| 3,651,799 | 3/1972 | Daynard | 128;419 PT/ |
| 3,662,746 | 5/1972 | Saltzberg et al. | 128/710 |
| 3,669,120 | 6/1972 | Nielsen | 128/419 PG |
| 4,000,461 | 12/1976 | Barber et al. | 128/708 |
| 4,117,848 | 10/1978 | Naylor | 128/419 PT |

Primary Examiner—William E. Kamm

Attorney, Agent, or Firm—Orrin M. Haugen; Thomas J. Nikolai

[57] ABSTRACT

An electronic interface module for use with patient monitoring equipment which allows use of the monitoring equipment at the same time that the patient is being treated through the application to his body of electrical stimulating pulses or the like. Body contacting leads used to pick up physiologically generated impulses from the body of the patient are coupled through a suitable amplifier to a sample and hold circuit. The interface module also includes means for generating a control pulse at the onset of a body stimulating impulse which control pulse persists for a predetermined time greater than the period of the stimulating impulse. This control pulse is also applied to the sample and hold circuit. The output from the sample and hold circuit (which may be analog or digital in nature) is, in turn, coupled through suitable matching circuitry to the patient monitoring equipment. The interface module thus eliminates the transmission of the stimulating impulses through the body contacting leads to the patient monitoring equipment while permitting the physiological electrical impulses to be transmitted to the monitoring equipment substantially without any significant change in waveform.

6 Claims, 5 Drawing Figures

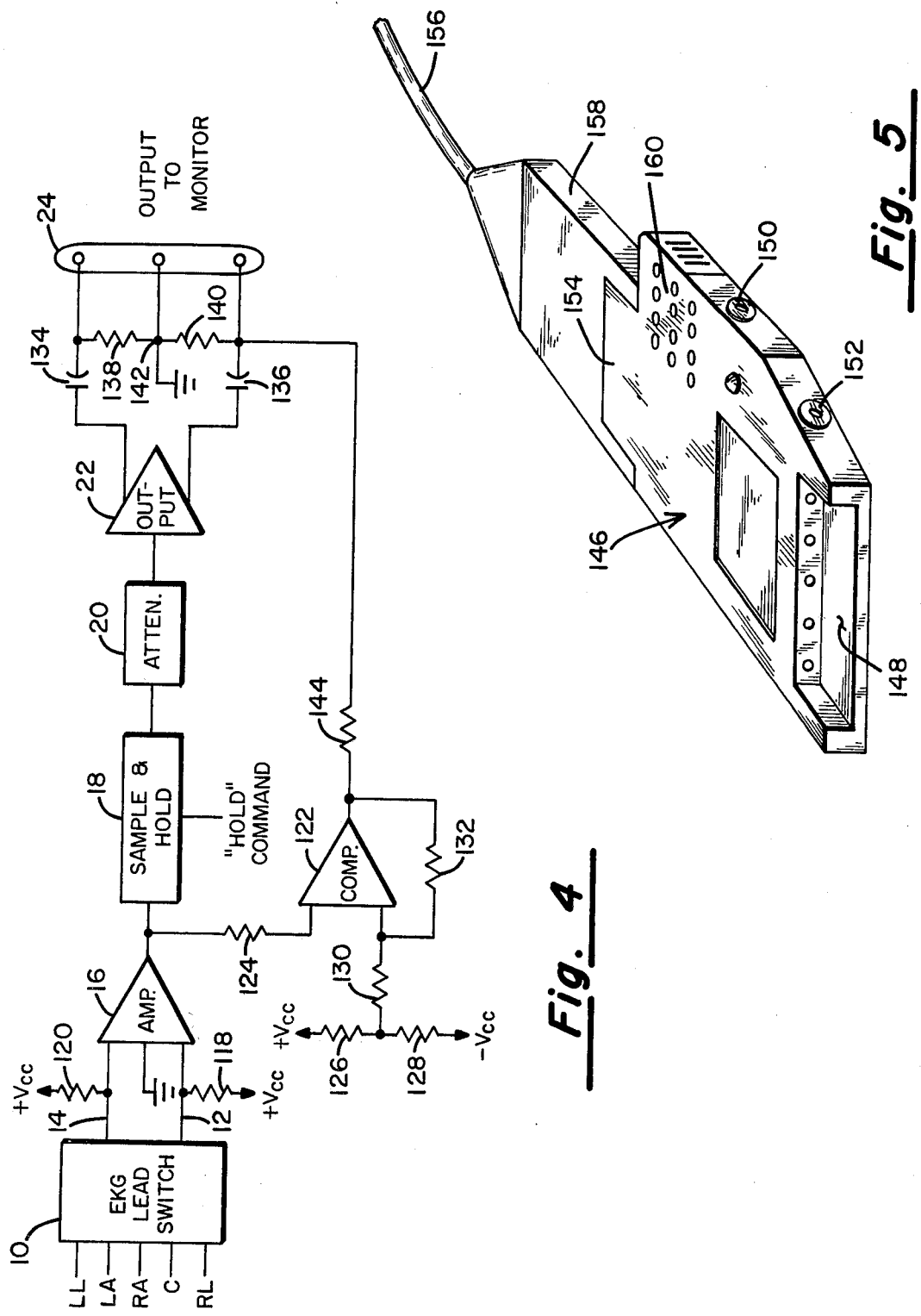

ELECTRONIC CIRCUIT PERMITTING SIMULTANEOUS USE OF STIMULATING AND MONITORING EQUIPMENT

BACKGROUND OF THE INVENTION

I. Field of the Invention

This invention relates generally to electromedical circuit apparatus and more specifically to an electronic interface module which is adapted to be coupled between conventional body contacting electrodes and patient monitoring equipment, the interface module acting to suppress or eliminate any aberration which may be superimposed upon the physiological signal being detected by externally applied body tissue stimulating impulses.

II. Discussion of the Prior Art

It is now quite commonly known that a transcutaneous electronic nerve stimulator (TENS) device may be used following surgery for the treatment and suppression of pain. In a typical TENS device, electrical impulses of predetermined frequency, amplitude and pulse width are generated and applied to the body of a patient proximate the locus of the pain by way of body contacting electrodes.

In modern post-operative intensive care units various vital signs are continuously monitored by automatic equipment in such a way that trained personnel at a central station are able to obtain an immediate indication of variations in such vital signs for a large number of patients. For example, following thoracic surgery, the patient is wired with suitable body contacting electrodes such that his EKG trace can be monitored at a nurse's station. Heretofore it has not been possible to treat a patient whose EKG trace is being monitored with a TENS device because the regularly applied stimulating pulses used for suppressing post-operative pain would feed through the body tissue to the patient contacting electrodes and would be picked up by the monitoring equipment. The strong stimulating signal would normally overload the sensitive amplifiers used in the monitoring equipment which could result in severe distortion of the waveforms being monitored to the extent that they become useless as a diagnostic tool. For example, the physiological signal comprising the EKG trace is routinely less than 0.001 volt. The TENS signal applied to the patient's skin is typically greater than this signal by a factor of up to 200,000.

Further, typically the body stimulating pulses from the TENS unit are of a substantially higher repetition rate than the PQRST complex of the typical EKG trace. As such, if one were to attempt to monitor the EKG trace while the patient is undergoing treatment with a TENS unit, one would find very high amplitude spikes superimposed upon the EKG trace. Depending upon the type of patient monitor being used, these spikes may appear as a fogging of the EKG signal and in displays employing cathode ray tubes of longer persistence, the presence of the stimulating impulses superimposed upon the EKG trace may cause complete obliteration of the cardiac signal.

Thus, if one is to effectively treat the patient with electrical stimulating pulses at the same time that it is desired to continuously monitor the patient's physiological processes, it becomes necessary to devise a way in which the body stimulating impulses can be discriminated and blocked so that they do not reach the display portion of the monitoring equipment.

In typical electrocardiographic equipment, highly sensitive direct coupled amplifiers are commonly employed to magnify the minute electrical signals comprising time varying voltages, which are generated by the body so that these signals may be recorded and/or observed. A difficulty in using such high sensitivity instruments is that in addition to the desired signal, there may be extraneous interfering signals and noise superimposed upon the desired signal which tend to obscure, distort or even overshadow the desired signal by reason of their magnitude, to such an extent that the value of the record of the desired signal is substantially decreased. In attempts to correct this situation, prior art approaches have relied upon frequency discrimination (filtering) or signal cancellation in which the interference signal is amplified and inverted in phase so that the resulting mirror signal can be used to cancel out the original interference signal.

These prior art techniques for cancelling noise components of a desired signal which are found in present day patient monitoring equipment are found to be ineffective in dealing with the intentionally applied body stimulating impulses used in the treatment of post-operative pain. Because of the direct application of the stimulating impulses to the body of the patient by way of skin contacting electrodes, the magnitude of the pulses picked up by the monitoring electrodes is so large in comparison to the physiological signal being measured thereby that the electronic equipment designed to respond only to the physiuological signals tends to be swamped out.

The purpose of the present invention is to provide an electronic interface module that will permit patient monitoring to take place simultaneously with the treatment of the patient involving the application of relatively high frequency stimulating impulses to the patient such as with a TENS device. Through the use of the module comprising the present invention it is possible to recover the relatively low level physiological signal even when buried in the much higher amplitude, much more rapid stimulator pulses.

SUMMARY OF THE INVENTION

In its simplest form, the present invention comprises an electronic device capable of sensing the onset or leading edge of a body stimulating pulse and disabling the patient monitoring equipment at that instant. The physiological signal being monitored is blocked from reaching the monitor display until the stimulating pulse terminates. In this way, the stimulator signal is prevented from entering the patient monitoring equipment entirely. Rather than merely turning off the EKG monitoring equipment upon detection of a stimulator pulse, the circuit of the present invention samples the amplitude of the physiological signal being measured at the leading edge of the stimulating impulse and holds a quantity indicative of the voltage level of the physiological signal at the sampling time until the stimulation pulse has terminated. The physiological signal being monitored is then allowed to proceed from the voltage level attained by the physiological signal at the sampling time rather than from a zero baseline. Because of the sample and hold technique employed and the "smoothing" afforded by the output circuitry of the preferred embodiment, the patient monitoring display circuitry responds without reflecting a chopped characteristic which might otherwise distort the monitored waveform to the point that it would no longer be suitable for diagnostic purposes.

The apparatus of the present invention therefore comprises an electronic module having input jacks adapted to be connected to the usual patient monitoring electrodes as well as additional jacks which permit the interface module to receive signals from the body stimulator. Further, a set of output jacks are provided for coupling the interface module to the conventional monitoring equipment used to display physiological signals. Contained within the interface module itself is an input amplifier structure which greatly amplifies the signals picked up on the patient monitoring electrodes and couples the amplified signals to a sample and hold circuit. The signal derived from the body stimulator pulse generator is coupled to a monostable multivibrator. Upon detection of the leading edge of a stimulator pulse, the one-shot circuit is triggered to its metastable state for a duration determined by the parameters of the circuit. This duration is adjusted so as to just exceed the pulse duration of the stimulator impulse applied to the patient. The output from the monostable multivibrator or one-shot is, in turn, applied to the "hold" input of the sample and hold circuit. So long as the one-shot remains in its metastable state, the output from the sample and hold circuit will be held at the level that the input thereto was at at the beginning of the hold command. Thus, when the output from the one-shot again reverts to its stable level, the sample and hold circuit will be released and the output from that circuit will resume at the value reached just before turn-off. The output from the sample and hold circuit is applied through an attenuator network and a combination of operational amplifiers to again convert the output signals from a single-ended output to a differential output which is compatible with the monitoring equipment.

By using the circuit of the present invention, the physiological signals from the patient can continue to be monitored even while electrical stimulating pulses are being applied to the patient. The interface circuit of the present invention introduces only a very slight notching of the physiological waveform, this distortion being so small that it requires no additional filtering or smoothing.

OBJECTS

It is accordingly the principal object of the present invention to provide a new and improved circuit module for interfacing the body contacting leads of a patient monitor/recorder to the monitoring/recording equipment itself in such a way that monitoring and/or recording of physiologically generated waveforms can continue while electrical impulses are applied to the body of the patient from an external source.

Another object of the invention is to provide a means whereby a patient can have his vital signs monitored while undergoing treatment involving the application of externally applied electrical impulses to his body.

Yet another object of the invention is to provide an electronic circuit module for effectively removing from a monitored waveform the signals attributable to externally applied electrical pulses.

Yet still another object of the present invention is to provide a relatively low cost but highly reliable module permitting simultaneous treatment through the application to the body of externally applied electrical signals and monitoring of internally generated physiological signals.

These and other objects and advantages of the invention will become apparent to those skilled in the art from the following detailed description of the preferred embodiment when considered in conjunction with the accompanying drawings in which like numerals in the several views refer to corresponding parts.

DESCRIPTION OF THE DRAWINGS

FIG. 4 is an electrical schematic diagram of a modification of the preferred embodiment; and FIG. 5 illustrates the manner in which the interface module of the present invention may be packaged to facilitate its use in the intended fashion.

DESCRIPTION OF THE PREFERRED EMBODIMENT

As is indicated in the introductory portion of this specification, transcutaneous electronic nerve stimulator devices have found wide application in the control and alleviation of chronic pain and in post-operative situations where the application of electrical stimulating signals to electrodes placed proximate to the incision site is found to substantially reduce the discomfort normally accompanying such surgery. A TENS device, such as disclosed in the Miller et al U.S. Pat. No. 4,121,594, typically includes a pulse generator capable of producing pulse type stimulating signals of adjustable frequency, width and amplitude. These pulses are applied to the body of the patient through leads connecting to electrodes which are adhesively secured to the skin of the patient proximate to the wound site.

In most hospital recovery rooms and intensive care units, electronic apparatus of one type or another is used to continuously monitor the vital signs of the patient either at bedside or at a central station. For example, equipment is provided whereby a nurse at a central station may view the EKG trace obtained from the patient via properly placed electrodes feeding conventional EKG monitoring equipment. However, if one attempts to utilize a TENS device or other apparatus in which externally applied electrical energy is applied to the patient's body while the monitoring process is going on, a difficulty arises due to the transmission through the body of the patient of the externally applied stimulating signals which reach the pick-up electrodes feeding the monitor.

Figure 1:
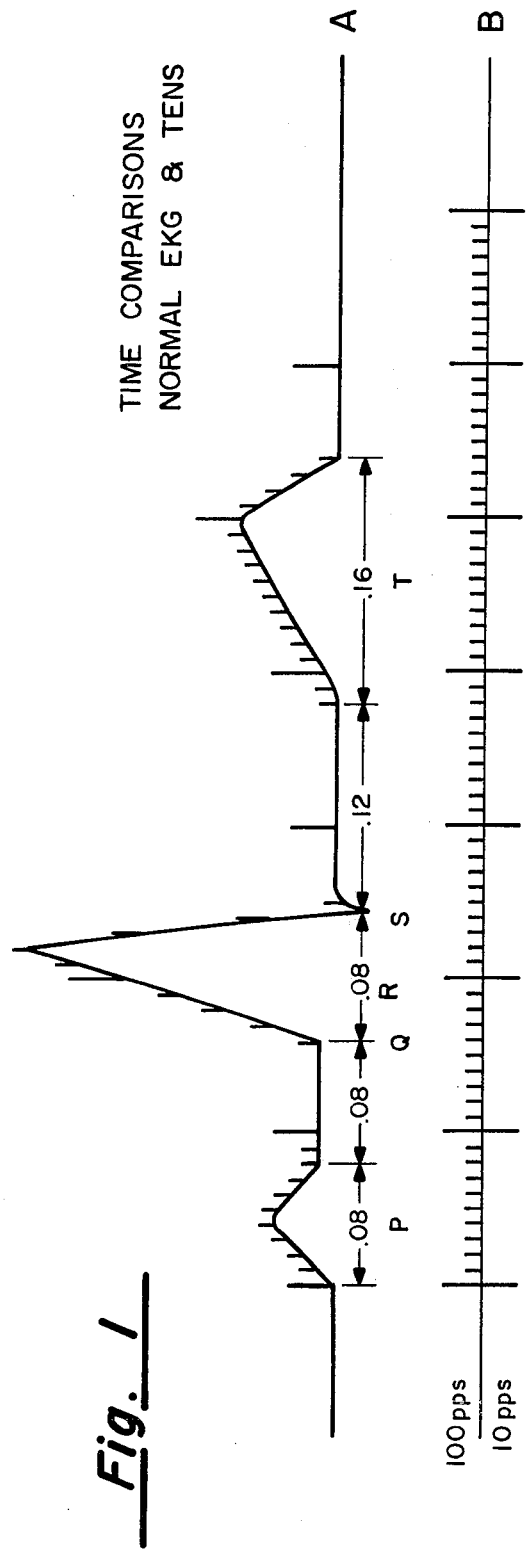
FIG. 1 is a diagram illustrating the nature of the waveform obtained from patient monitoring electrodes when externally applied electrical impulses are applied to the patient, the impulses being greatly reduced in amplitude.

Referring to FIG. 1, there is shown in Line B the output from a TENS device operating in one instance at a frequency of 10 pulses per second and another at 100 pulses per second. The time scale for the waves of lines A and B of FIG. 1 is shown in Line C of FIG. 1. Because a typical output pulse from a TENS device will have a pulse width in the range of from 50 to 1,000 microseconds, these pulses appear as a straight vertical line when drawn to the time scale of FIG. 1C. The waveform of FIG. 1A represents the resulting signal pattern when stimulator pulses of FIG. 1B are superimposed on a typical EKG PQRST complex. While in FIG. 1A the externally applied stimulator pulses are represented by short vertical spikes, it is to be understood that these spikes are typically $10^5$ times the amplitude of the detected EKG wave. The presence of the large amplitude, relatively high frequency TENS pulses in the monitoring equipment may so distort and overdrive the circuitry employed therein that the underlying EKG waveform cannot successfully be monitored. It is the purpose of the present invention to obviate this problem and permit the simultaneous treatment of a patient with externally applied electrical impulses while monitoring physiological signals derived from the body of the patient. This is accomplished through the utilization of an electronic interface module which may be physically connected between the pick-up electrodes coupled to the patient and the conventional monitoring equipment utilized for displaying the physiological signals obtained. A block diagram of this module is shown in FIG. 2.

Figure 2:
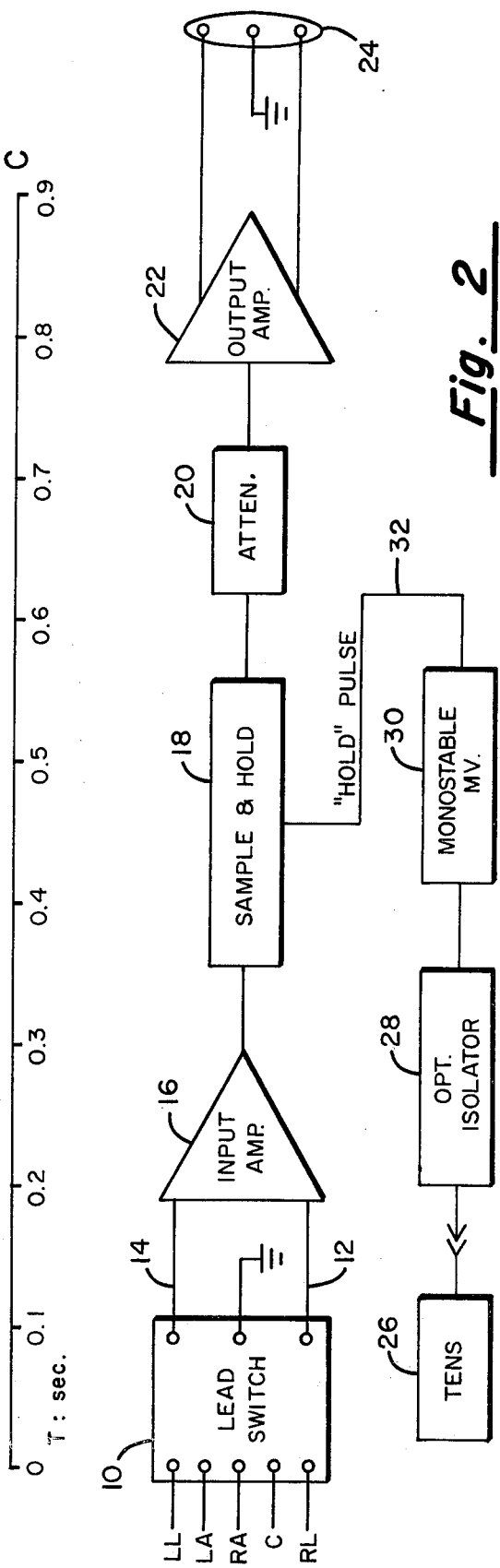
FIG. 2 is a block diagram illustrating the principles of the present invention.

With reference to FIG. 2, there is shown a switching device 10 which is conventional in all respects and which is designed to selectively connect sets of pick-up electrodes to the input terminals 12 and 14 of an input amplifier 16. For purposes of illustration only, the preferred embodiment is being described in an application wherein EKG signals are the physiological signals being monitored. It is to be understood, however, that the system would be equally applicable to an electroencephalograph, to electromyograph signals emanating from muscle tissue or to other types of physiologically produced emfs. In EKG equipment, there are typically pick-up electrodes associated with the left leg, left arm, right arm, chest and right leg. The signals induced in these pick-up electrodes are selectively applied as inputs to the switch 10 as indicated by the corresponding initials on the incoming lines.

The input amplifier 16 magnifies the minute incoming signals from the electrodes to a level compatible with the sample and hold (S & H) circuit 18 to which the input amplifier 16 is connected in a driving relationship. As will be described more fully hereinbelow, the input amplifier is designed to provide a high common mode noise rejection ratio.

Assuming simultaneous use of body stimulation equipment and EKG monitoring equipment, the signal reaching the input of the S & H circuit 18 is as depicted in FIG. 1A of the drawings. The single ended output from the circuit 18 is applied through an attenuator network 20 to the input terminals of an output amplifier stage 50 which serves to match the output from the interface module to the input of the standard monitoring equipment with which the present invention is used. In this regard, the attenuator 20 and output amplifier 22 are designed to reduce the gain introduced into the system by the input amplifier 16 and also provide a differential type output at the terminals 24. It is to these last-mentioned terminals that the standard monitoring equipment is connected by a suitable cable or otherwise.

Also shown in the block diagram of FIG. 2 is a device used for applying electrical stimulating pulses to the body of the patient, here shown as a TENS unit 26. The output signals from the TENS unit 26 are coupled through a protection circuit which may, for example, include an opto-isolator device of conventional design, to the trigger input terminal of a monostable multivibrator or one-shot circuit 30. The output from the one-shot circuit 30 is connected by a conductor 32 to the "hold" input terminal of the S & H circuit 18. As is well known in the art, once a one-shot circuit is triggered, it remains in a metastable state for a time interval determined by the electrical components thereof and once this period has elapsed, the output automatically reverts to a potential level at which it remains until again triggered. In the present application, the one-shot circuit 30 is triggered by the leading edge of the pulse produced by the TENS unit 26 and it persists in its metastable state for a period of time which is slightly greater than the pulse width of the output from the TENS unit 26. The signal applied to the S & H network 18 on the conductor 32 causes its output to be held at the same voltage level which existed at the input of the network at the onset of the control pulse for the entire duration of the control pulse. Hence, when the monostable multivibrator circuit 30 again reverts to its stable state, the output from the S & H circuit 18 will continue from that level rather than from the zero baseline which would be the case if conventional switching had been employed. In that the pulse width of the TENS output is very short compared to the width of the signals comprising the PQRST complex of the physiological wave being monitored, the spikes appearing on the waveform of FIG. 1A are effectively blanked out without introducing a significant or noticeable discontinuity in the EKG waveform.

Having described the general organization and mode of operation of the interface module of the present invention, consideration will next be given to the details of the preferred embodiment thereof. In this regard, reference will be made to the detailed electrical schematic diagram set forth in FIG. 3 of the drawings.

The input amplifier stage 16 of FIG. 2 comprises first, second and third operational amplifiers 34, 36 and 38 respectively. The operational amplifier 34 has its non-inverting input coupled through resistors 40 and 42, to the input terminal 14. Similarly, the input terminal 12 is coupled through a divider, resistors 44 and 46, to the non-inverting input of operational amplifier 36. Resistors 40 and 44 protect the amplifiers while resistors 42 and 46 establish the input impedance of the amplifiers 34 and 36, respectively. Coupled between input lines 12 and 14 are diode clamping networks 48 and 50 which protect the amplifiers from excessive voltage swings which might be occasioned by the body stimulating pulses picked up by the monitoring electrodes.

The output from the operational amplifier 34 is coupled through a feedback resistor 52 to the inverting input thereof and, similarly, the output from operational amplifier 36 is coupled through a feedback resistor 54 to its inverting input. A resistor 56 is connected between the inverting inputs of the operational amplifiers 34 and 36 and is used to set the gain of the combined stage, 34 and 36.

The output from the operational amplifier 34 is coupled through a resistor 58 to the inverting input of the amplifier 38. The output from operational amplifier 36 is coupled through a resistor 60 to the non-inverting input of the operational amplifier 38. A feedback resistor 62 connects the output from this last-mentioned operational amplifier back to its inverting input while a resistor 64 is connected between the non-inverting input of that amplifier and a point of fixed potential (ground). Through the proper choice of component values for the various resistors mentioned, the input amplifier 16 can be made to exhibit an input impedance of approximately 10 megohms and a common mode rejection ratio of 100 db while exhibiting an overall gain of 1,000. The common mode rejection ratio achieved is dependent upon proper balance or matching of the resistive components mentioned. By making resistor 56 variable, the precise gain of the amplifier may be adjusted to meet desired requirements.

The sample and hold circuit 18 employed may, for example, be an Analog Devices type AD 582 integrated circuit which is connected in a manner described in the manufacturer's specification sheets for that product. It receives at its input pin 1 the output from the operational amplifier 38 via a coupling circuit including capacitor 66 and resistor 67. The output from the S & H circuit 18 is obtained at pin number 8 to which the resistive attenuator network 20 is connected. Also connected to the output pin of the S & H circuit 18 is a resistive voltage divider including resistors 68 and 70. As is explained in the manufacturer's specification sheets, the resistors 68 and 70 determine the overall gain of the circuit 18. That is, the gain of the S & H circuit is equal to $R_{70}/R_{68}$.

The circuit 18 switches off the EKG signal during the interval when the externally applied pulse from the TENS unit is passing through the body tissues. Simultaneously, it maintains the level of the EKG signal existing at the time of triggering and prevents this voltage value from returning to zero during the blocking interval. The storage element in this circuit is the holding capacitor 72 connected to pin 6 of the S & H integrated circuit chip. This capacitor also functions as a low level filter in reducing any notching effect which might otherwise distort the EKG waveform.

While the Type AD 582 S & H circuit mentioned above is analog in nature, those skilled in the art will recognize that the S & H function can be implemented using digital logic. For example, an analog-to-digital converter can be used to generate a digital quantity representative of the amplitude of the physiological signal at the instant the leading edge of an externally applied signal is detected. This value may be stored in a register for a predetermined time and then applied via a digital-to-analog converter to the module's output section.

Figure 3:
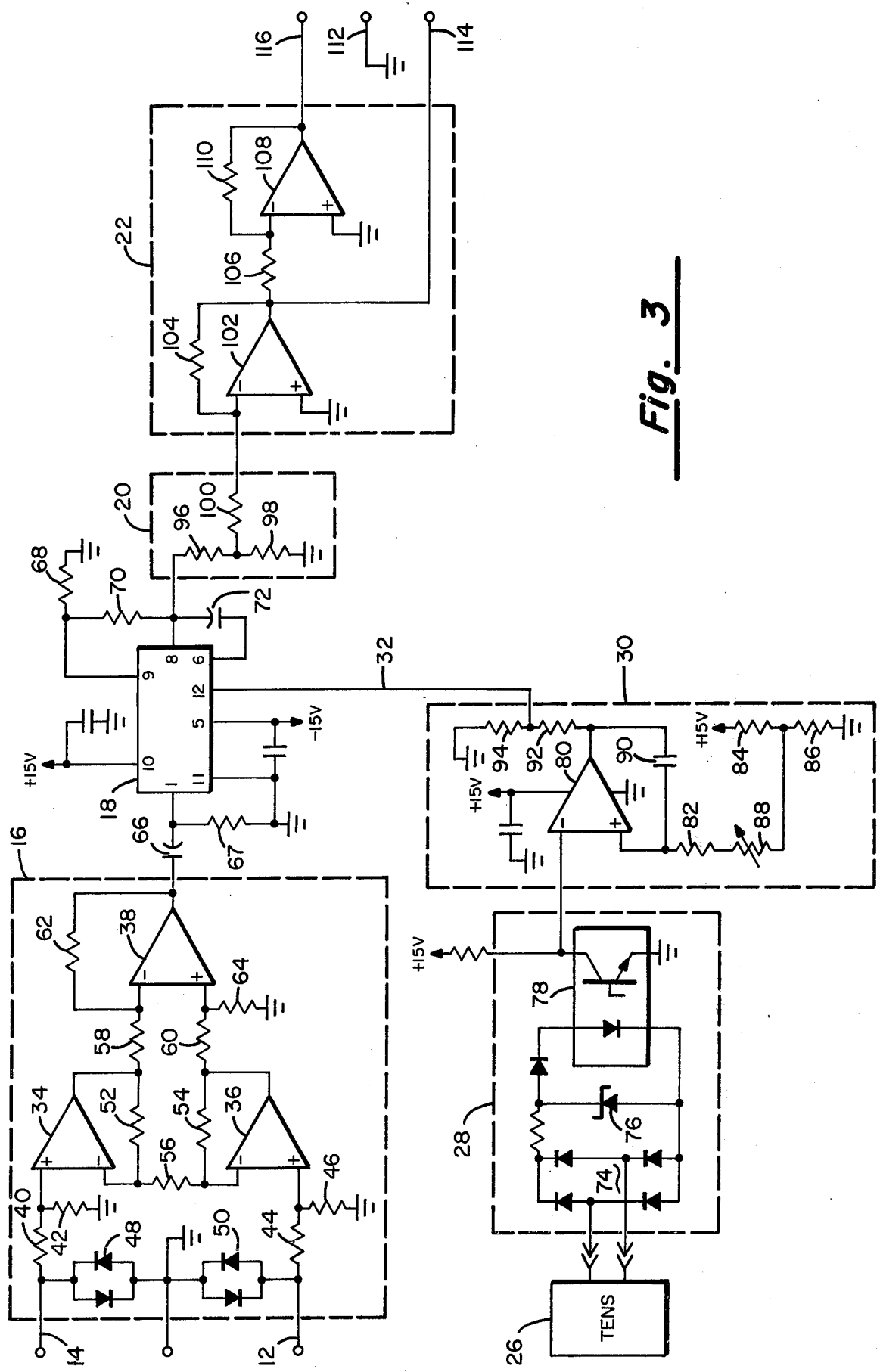
FIG. 3 is an electrical schematic diagram of one implementation of the block diagram of FIG. 2.

The trigger circuit used to control the S & H circuit 18 includes the protection circuit 28 and the one-shot circuit 30. As is illustrated in FIG. 3, the protection circuit includes a full-wave rectifier bridge circuit 74, a Zener diode 76 and an opto-isolator unit 78. A first set of terminals of the rectifier bridge 74 is coupled to the output electrodes of the TENS pulse generator 26 and functions to convert the bi-polar pulse therefrom to a singular polarity pulse. Most TENS units on the market utilize an output transformer and the Zener diode circuit 76 clips the flyback pulse from that transformer to safe levels and thereby protects the components of the opto-isolator 78. The opto-isolator 78 is employed in the triggering circuit of the one-shot so that the one-shot will not be adversely affected by cross-talk signals emanating from the TENS unit.

The output from the opto-isolator 78 is connected to the inverting input of an operational amplifier 80 whose non-inverting input is coupled through a resistive voltage divider including fixed resistors 82, 84 and 86 and variable resistor 88. More specifically, connected between a source of positive potential and ground is a voltage divider including resistors 84 and 86. The common terminal between these two resistors is coupled through a series combination of the variable resistor 88 and the fixed resistor 82 to the non-inverting input terminal of the operational amplifier 80. A capacitor 90 is connected as a feedback component from the output terminal of the operational amplifier 80 back to its non-inverting input. Those skilled in the art will recognize that this combination of elements just described functions as a monostable multivibrator or one-shot circuit. The period of instability of the one-shot circuit is determined primarily by the variable resistor 88 and the capacitor 90. In the present application, it is desirable that the pulse width from this multivibrator be variable and typically in the range of from 500 to 3,000 microseconds. However, the pulse width is determined by the expected width of the stimulating pulse from the TENS unit used.

Coupled between the output terminal of the operational amplifier 80 and a point of fixed potential (ground) is a voltage divider including resistors 92 and 94. The "hold" signal applied to pin 12 of the S & H circuit 18 is obtained at the common junction between these last-mentioned resistors. The output resistors 92 and 94 serve to reduce the output voltage swing from the multivibrator to levels appropriate to the S & H circuit 18.

As has been mentioned, the output from circuit 18 is coupled through the attenuator 20 to an output circuit 22. The attenuator network includes the resistors 96 and 98. Resistors 96 and 98 are connected in series between the output terminal (pin 8) of circuit 18 and ground. The common junction between resistors 96 and 98 is connected through resistor 100 to the inverting input terminal of an operational amplifier 102. The non-inverting input of the amplifier is connected directly to ground and a feedback resistor 104 is coupled between the output terminal of circuit 102 and the inverting input thereof. The output from operational amplifier 102 is coupled through a resistor 106 to the inverting input terminal of still another operational amplifier 108. The non-inverting input of this amplifier is connected to ground and a feedback resistor 110 is coupled between the output thereof and the inverting input. A differential type output is obtained between the grounded terminal 112 and the output terminals from operational amplifiers 102 and 108, i.e., terminals 114 and 116, respectively.

The component value for the resistors 96 and 98 used in the attenuator depend upon the amount of amplification employed in the overall interface module. That is, to allow the EKG wave to drive the S & H circuit it was necessary to amplify the EKG signal significantly. Because the amplified output would not be compatible with the external monitoring circuitry, it becomes necessary to again reduce the overall gain of the interface module. The input impedance of the attenuator network must be designed so as not to unduly load down the output of the S & H circuit 18 and the output impedance of the attenuator network must be low in relation to the input impedance of the output amplifier 22.

The purpose of the output amplifier 22 is to convert the single-ended EKG signal emanating from the output terminal (pin 8) of the S & H circuit 18 to a differential signal compatible with the conventional patient monitoring device with which the present invention is intended to be used. Because two operational amplifiers 102 and 108 are used to obtain the differential output between terminals 114 and 116 and the grounded terminal 112, this arrangement provides an overall gain factor of 2. Hence, the attenuator network 20 is designed to apply to the input terminal of the operational amplifier 102 a signal which is one-half of the voltage originally applied to the input terminals 12 and 14 of the input amplifier stage 16. When this is done, the EKG output signal from the interface circuit will be substantially equal in amplitude to the EKG signal applied to its input. Hence, the output signal will be fully compatible with the external monitoring equipment with which the present invention is used.

It has also been found desirable to provide circuitry in the interface unit for signaling improper lead connections. That is to say, most present day patient monitoring equipment of the type with which the present invention finds use includes circuitry for indicating EKG lead open circuits arising from broken wires, loosened or detached electrodes, or dry-gel connections leading to very high skin resistances. Typically either audible and/or visual signaling devices are associated with the monitor to alert medical personnel to this condition. Hence, the medical personnel will be apprised as to whether the loss of EKG waveform presentation is due to an equipment problem or to a failure of the heart in the patient being monitored.

FIG. 4 illustrates by means of an electrical schematic diagram a modification which may be made to the circuit depicted in the block diagram of FIG. 2 so as to preserve the lead fault detection feature.

The modification to the circuit of FIG. 2 (as reflected in FIG. 4) involves the addition of two equal resistors 118 and 120 which are coupled between a source of positive potential Vcc and the input lines 12 and 14 to the input amplifier 16 respectively. In addition, a comparator network is provided including the comparator 122 which has a first input thereof coupled by way of a resistor 124 to the output of the input amplifier 16. The second input to the operational amplifier 122 establishes the trip point for the comparator. Specifically, a resistive voltage divider network including resistors 126 and 128 is connected across a balanced DC supply and the common point between these two resistors is coupled through a resistor 130 to the second input terminal of the operational amplifier 122. A feedback resistor 132 joins the output of the operational amplifier back to this second input terminal.

The modification incorporating the fault detection feature also includes the network coupled across the output leads of the output amplifier 22. As is illustrated in FIG. 4, disposed between the output amplifier 22 and the terminals 24 is a network including capacitors 134 and 136 and resistors 138 and 140. The upper lead of the amplifier 22 is coupled through the capacitor 134 and the resistor 138 to ground at junction 142. Similarly, the lower lead of the output amplifier 22 is coupled through the capacitor 136 and the resistor 140 to that same grounded junction 142. Finally, a resistor 144 couples the output from the comparator network to one side of the output network just described. That is, as is shown in FIG. 4, the resistor 144 couples the output of the comparator to the junction point between the capacitor 136 and the resistor 140.

The manner in which the lead fault detection circuitry operates can now be explained. The resistors 138 and 140 constitute DC current paths which prevent the continual operation of the alarm circuits in the monitor occasioned by the introduction of the interface module of the present invention between the patient leads (the input to the lead switch 10) and the monitor itself (not shown). In practice, these resistors 138 and 140 are to be closely matched in magnitude because of the fact that they influence the common-mode rejection of the monitor electronics. The resistors 118 and 120 coupled to the input lines of the input amplifier 16 are matched within a predetermined tolerance and because of their connection to the DC source, place a very low DC current (in the order of nanoamperes) on the patient leads through the switch 10. When the leads are properly connected to the patient, this current flows through the patient to the ground or common connection, usually associated with the electrode coupled to the right leg. Because of the low amplitude of this current, it is far too small to interfere with the physiological waveform being monitored or the operation of the TENS pulse generator.

The amplified output of the input amplifier 16 is connected through the resistor 124 to a first input of the comparator 122, whose other input is connected to a reference voltage designed to cause the comparator to switch when a predetermined voltage level appears at the input of the amplifier 16. The parameters of the comparator are designed such that its output is approximately zero volts when the patient electrodes are properly placed and coupled to the body of the patient. The output from the comparator 122 is coupled through resistor 144 to only one side of the output of the interface device. Thus, when the comparator senses a voltage output from the amplifier 16 which exceeds the predetermined reference, the comparator will drive only one of the monitor leads causing a predetermined voltage swing on that output lead. This voltage signal is designed to activate the alarm circuits (not shown) in the patient monitor system.

In the event of an electrode fault, the associated lead connecting that electrode to the input amplifier 16 will essentially see an open circuit and the loss of the sinking for the current provided through the resistor 118 or 120. Hence, the input voltage on the lead associated with the faulty electrode will be found to rise to a predetermined value above the voltage reference applied via resistor 130 to the comparator 122. This amplified value of the fault voltage causes the comparator to switch, thereby unbalancing the input to the patient monitor, as previously described, and triggering its alarms.

For the sake of completeness, but with no limitation intended, the following component values may be employed in implementing the interface module of the present invention. Because in many instances the absolute value of the components in question is not as critical as is the fact that the components be properly matched, limitation to the precise values set out is not necessary.

TABLE I

| | |
|---|---|
| $R_{40} = R_{44}$ | 12.1 kohms |
| $R_{42} = R_{46}$ | 10 mohms |
| $R_{56}$ | 2 kohms |
| $R_{52} = R_{54}, R_{62} = R_{64}, R_{67}, R_{70}$ | 100 kohms |
| $R_{58} = R_{60}, R_{68}, R_{92}$ | 10 kohms |
| $R_{96}$ | 1 mohm |
| $R_{98}$ | 51 ohms |
| $R_{100} = R_{104} = R_{106} = R_{110}$ | 18.2 kohms |
| $R_{82}$ | 220 kohms |
| $R_{84}$ | 120 kohms |
| $R_{86}$ | 47 kohms |
| $R_{88}$ | 2.5 mohms - var. |
| $R_{94}$ | 4.3 kohms |
| $C_{72}$ | 1 uf |
| $C_{90}$ | .0051 uf |
| Op-Amps 34, 36, 38, 80, 102, 108 | Type PM - 308 A |
| S & H circuit | Type Ad 582 |
| $R_{138} = R_{140}$ & $R_{120} = R_{118}$ | |

FIG. 5 illustrates one arrangement whereby the electronic circuits comprising the interface module may be packaged. However, since various other arrangements may be devised for housing the circuitry while providing access to the electrical input and output jacks, no limitation to the illustrated structure should be inferred. The housing is indicated generally by numeral 146 and may be formed from a suitable insulating plastic material. The EKG input leads and lead switch assembly (not shown) is adapted to be plugged into the receptacle 148. Contained within the housing 146 are the input amplifier 16, the S & H circuit 18, the attenuator 20, the output amplifiers 22, the protection circuit 28 and the one-shot circuit 30. These components may be mounted on a printed circuit board in a conventional fashion. A coaxial jack 150 is provided for receiving the output pulses from the TENS unit 26, these pulses being utilized by the one-shot circuit for developing the necessary "hold" signal for the S & H circuit 18. A second jack 152 is provided such that the stimulating pulse may be fed out of that jack and via a coaxial lead (not shown) to the electrode used for applying the stimulating impulses to the body tissue of the patient.

The housing 146 may also contain space for locating batteries for powering the active components of the interface module. The housing 146 further includes a connector assembly indicated by numeral 154 which is designed to couple with the differential input leads of the monitor device. The cable leading to the monitor (not shown) is identified by numeral 156 and its connector for mating with the interface module is identified by numeral 158.

While the alarm circuits for detecting open or intermittent leads and/or pick-up electrodes would normally be located in or around the monitoring electronics, it may also be desirable to include an audio alarm within the interface module itself so that this alarm may be used during the initial placement of the electrodes and leads on the body of the patient. While the transducer portion of this audio alarm is not shown, the housing 146 is illustrated as containing a set of apertures 160 in a surface thereof for permitting sound waves to exit from the housing.

Thus it can be seen that there has been described the preferred embodiment of the present invention. Various modifications and changes will occur to those skilled in the art upon a reading of the instant specification and through an examination of the drawings. Accordingly, the scope of the invention is to be determined solely from the appended claims.

What is claimed is:

1. An electronic circuit for permitting simultaneous use of patient monitoring equipment and body tissue stimulating equipment, comprising:
    (a) first input means for receiving physiologically generated signals from the body of a patient;
    (b) second input means for receiving electrical stimulation signals applied to said patient, said electrical stimulation signals being of a substantially higher frequency and amplitude than said physiologically generated signals;
    (c) a sample and hold circuit coupled to said first and second input means for temporarily interrupting the transmission of said physiologically generated signal to store a quantity proportional to the amplitude of said physiologically generated signal at a time coincident with the onset of one of said electrical stimulation signals and for resuming the transmission of said physiologically generated signal from a voltage level defined by said quantity following the termination of said electrical stimulation signal; and
    (d) an output circuit means coupled to the output terminal of said sample and hold circuit and adapted to be coupled to said patient monitoring equipment for matching the amplitude of the signals appearing at the output terminal of said sample and hold circuit to a level compatible with said patient monitoring equipment.

2. Apparatus as in claim 1 wherein said first input means comprises:
    (a) amplifier means having differential input terminals adapted to be selectively connected to body contacting electrodes, and an output terminal coupled to said sample and hold circuit.

3. Apparatus as in claim 1 wherein said second input means comprises:
    (a) a monostable multivibrator circuit having a trigger input terminal and an output terminal;
    (b) means adapted to couple said electrical stimulation signals to said trigger input terminal for switching said monostable multivibrator to its metastable state on the leading edge of said stimulation signals; and
    (c) means coupling said output terminal of said monostable multivibrator to said sample and hold circuit.

4. Apparatus as in claim 3 wherein, once triggered, said monostable multivibrator remains in said metastable state for a predetermined period approximately equal to, but greater than, the period of said electrical stimulation signal.

5. Apparatus as in claim 3 wherein said means adapted to couple said electrical stimulation signals to said trigger input terminal comprises:
    (a) a full-wave rectifier adapted to receive the output from said body tissue stimulating equipment for producing single polarity pulses therefrom;
    (b) clamping means coupled to said full-wave rectifier for limiting the amplitude of said single polarity pulses; and
    (c) an opto-isolator circuit coupled between said clamping means and said trigger input terminal of said monostable multivibrator.

6. Apparatus as in claim 1 wherein said output circuit means comprises:
    (a) signal attenuator means connected to said output terminal of said sample and hold circuit for reducing the amplitude of the signals emanating from said sample and hold circuit; and
    (b) first and second operational amplifier circuits connected to said signal attenuator means for producing a differential input signal from the single-ended output signal from said sample and hold circuit, said differential input signal being adapted to be applied to said patient monitoring equipment.

* * * * *